(12) United States Patent
Skoglund et al.

(10) Patent No.: US 11,350,649 B2
(45) Date of Patent: Jun. 7, 2022

(54) FLASH BOILING APPARATUS

(71) Applicant: Tetra Laval Holdings & Finance S.A., Pully (CH)

(72) Inventors: Tomas Skoglund, Lund (SE); Fredrik Innings, Torna Hällestad (SE); Martin Erixon, Limhamn (SE); Sandra Nilsson, Lerberget (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 32 days.

(21) Appl. No.: 16/470,273

(22) PCT Filed: Dec. 19, 2017

(86) PCT No.: PCT/EP2017/083507
§ 371 (c)(1),
(2) Date: Jun. 17, 2019

(87) PCT Pub. No.: WO2018/122036
PCT Pub. Date: Jul. 5, 2018

(65) Prior Publication Data
US 2020/0008450 A1 Jan. 9, 2020

(30) Foreign Application Priority Data
Dec. 29, 2016 (SE) .................................. 1600355-0

(51) Int. Cl.
*A23L 3/18* (2006.01)
*A23L 3/00* (2006.01)
(Continued)

(52) U.S. Cl.
CPC ................. *A23L 3/18* (2013.01); *A23L 3/001* (2013.01); *A23L 3/015* (2013.01); *A23L 3/22* (2013.01); *A47J 31/00* (2013.01); *A23C 3/037* (2013.01)

(58) Field of Classification Search
CPC ... A23C 3/037; A23L 3/16; A23L 3/18; A23L 3/22
(Continued)

(56) References Cited
U.S. PATENT DOCUMENTS 5,415,764 A 5/1995 Van Der Piepen
6,513,422 B1 2/2003 Palm
(Continued)

FOREIGN PATENT DOCUMENTS

CN 205216242 U 5/2016
EP 2 540 365 A1 1/2013
(Continued)

OTHER PUBLICATIONS

International Search Report for corresponding Application No. PCT/EP2017/083507, dated Mar. 20, 2018.
(Continued)

*Primary Examiner* — Reginald Alexander
(74) *Attorney, Agent, or Firm* — Renner, Otto, Boisselle & Sklar, LLP

(57) ABSTRACT

A flash boiling apparatus for a liquid food product that includes particles, the apparatus including a vacuum vessel provided with a product inlet and a product outlet for liquid food product, a pressure relief valve arranged upstream the product inlet for providing a pressure drop that results in flash boiling of the liquid food product, and an inlet section arranged between the pressure relief valve and the product inlet, for conveying the liquid food product from the pressure relief valve to the product inlet. The inlet section includes a through-flow area that increases in a direction from the pressure relief valve to the product inlet, such that a flow velocity of the liquid food product decreases when it passes the inlet section.

15 Claims, 3 Drawing Sheets

(51) Int. Cl.
*A23L 3/015* (2006.01)
*A47J 31/00* (2006.01)
*A23L 3/22* (2006.01)
*A23C 3/037* (2006.01)

(58) Field of Classification Search
USPC ........... 99/453, 454; 422/1, 26, 39; 426/511, 426/520, 521, 522
See application file for complete search history.

(56) References Cited

U.S. PATENT DOCUMENTS

| | | | |
|---|---|---|---|
| 6,792,896 B2* | 9/2004 | Palm | A23C 3/037 122/19.1 |
| 9,011,953 B2* | 4/2015 | Kowalik | A23C 3/037 426/511 |
| 2004/0123814 A1 | 7/2004 | Palm | |
| 2012/0321771 A1 | 12/2012 | Kowalik | |
| 2016/0183549 A1 | 6/2016 | Innings | |
| 2018/0001281 A1* | 1/2018 | Skoglund | B01F 3/2021 |

FOREIGN PATENT DOCUMENTS

| | | |
|---|---|---|
| WO | 02/26346 A1 | 4/2002 |
| WO | 2015/036523 A1 | 3/2015 |
| WO | 2016/097278 A1 | 6/2016 |
| WO | 2016097280 A1 | 6/2016 |

OTHER PUBLICATIONS

Office Action and Search Report for corresponding Swedish Application No. 1600355-0, dated Jul. 25, 2017.
Jayanti, Bend, Flow and Pressure Drop in, A-to-Z Guide to Thermodynamics, Heat & Mass Transfer, and Fluids Engineering, Thermopedia, 2011 [retrieved Jul. 21, 2017]. Retrieved from <http://www.thermopedia.com/content/577/>.

* cited by examiner

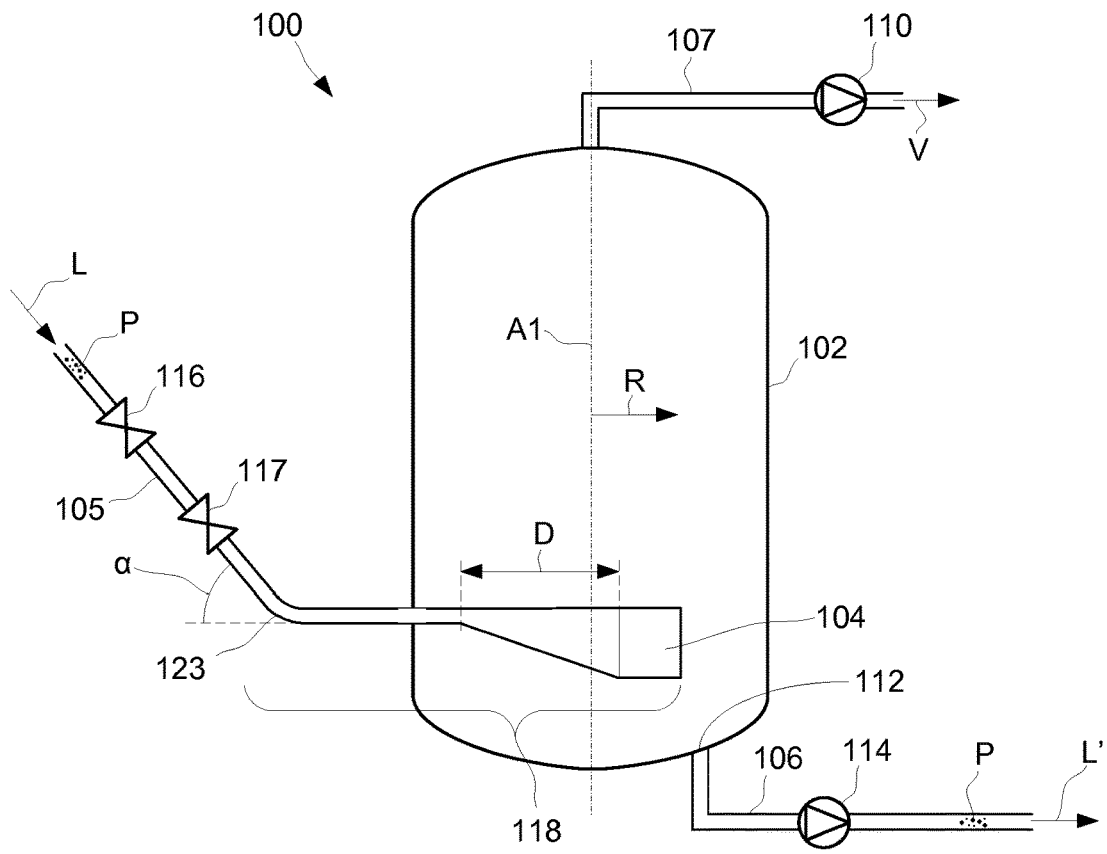
Fig. 1
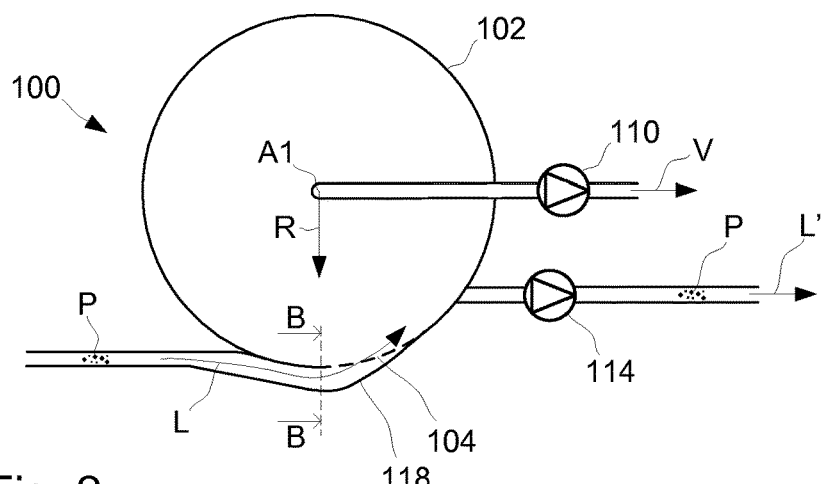
Fig. 2
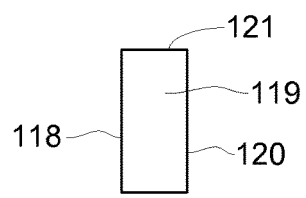
Fig. 3 (B-B)

FLASH BOILING APPARATUS

TECHNICAL FIELD

The present application relates to a flash boiling apparatus for liquid food products that comprises particles, a food processing system comprising the flash boiling apparatus, and a method for flash boiling liquid food products that comprises particles.

BACKGROUND ART

Today, in many liquid food processing systems a flash boiling stage may be included for a number of reasons. For example, when heat treating a liquid food product by steam injection for killing microorganisms, the product is held at a heat treatment temperature for a few seconds before it is introduced into a vacuum vessel to be flash boiled, or flash cooled. The flash boiling reduces the temperature of the product and removes an amount of vapour that equals the amount of steam that was injected for the heat treatment.

Flash boiling may also be used when it is desired to increase the concentration of a liquid food product. The product is then introduced in a vacuum vessel that acts as an evaporator, where vapour is removed by virtue of the flash boiling that takes place in the vessel.

Also, flash boiling of liquid food products takes place in so called deaerators where pre-heated product is fed to a vacuum vessel. The pressure of the product then drops and the product boils, such that gas that is dissolved in the product is expelled. Vapour that is created when deaerating the product is typically condensed into water that is returned to the product.

Flash boiling, also referred to as flash evaporation, is in brief the well known process where vapour is created when a saturated liquid stream undergoes a reduction in pressure by passing through a throttling valve or another type of throttling device. The throttling valve is typically located near the entry into the vacuum vessel so that the flash boiling (evaporation) occurs within the vessel.

As described, there are several reasons for flash boiling a liquid food product. Regardless of reason, a vacuum vessel is used and the liquid food product enters the vacuum vessel at a high speed. When entering the vacuum vessel the product typically impinges on or flow along an interior wall of the vacuum vessel. This impingement and/or flow may cause excessive wear of the vacuum vessel, in particular if the liquid food product comprises particles. To handle this problem the vacuum vessel must be regularly repaired or replaced, which increases operations costs and downtime.

Hence, there is a need for a flash boiling apparatus that can handle liquid food product comprising particles, while still providing long running times between service intervals.

SUMMARY

It is an object of the invention to at least partly overcome one or more of the above-identified limitations of the prior art. In particular, it is an object to provide a flash boiling apparatus that can handle liquid food product comprising particles and still provide long running time between service intervals.

Thus, a flash boiling apparatus for a liquid food product that comprises particles is provided. The flash boiling apparatus comprises a vacuum vessel that is provided with a product inlet for incoming liquid food product and a product outlet for outgoing liquid food product, a pressure relief valve that is arranged upstream the product inlet, for providing a pressure drop that results in flash boiling of the incoming liquid food product, and an inlet section that is arranged between the pressure relief valve and the product inlet, for conveying the liquid food product from the pressure relief valve to the product inlet. The inlet section comprises a through-flow area that increases in a direction from the pressure relief valve to the product inlet, such that a flow velocity of the liquid food product (L) decreases when it passes the inlet section.

The flash boiling apparatus is advantageous since the increased through-flow area of the inlet section reduces the flow velocity of the liquid food product. A reduced flow velocity reduces any wear that might take place after the liquid food product leaves the inlet section, i.e. when the liquid food product enters the vacuum vessel via the product inlet. Calculations have shown that a 50% reduction of the flow velocity of the liquid food product may reduce the wear of the vacuum vessel by up to 92%. It is harder to determine the exact wear during tests, but empirical studies of the flash boiling apparatus have shown that significant decrease and even elimination of wear may be accomplished by decreasing the flow velocity of the liquid food product.

According to another aspect a food processing system is provided. The food processing system comprises a steam injection device, a holding cell and the flash boiling apparatus previously described.

According to another aspect a method for flash boiling a liquid food product that comprises particles is provided. The method comprises: passing liquid food product through a pressure relief valve arranged upstream a product inlet of a vacuum vessel, for providing a pressure drop that results in flash boiling of the liquid food product when the liquid food product is introduced the vacuum vessel; passing the liquid food product through an inlet section that is arranged between the pressure relief valve and the product inlet, and comprises a through-flow area that increases in direction from the pressure relief valve to the product inlet, such that a flow velocity of the liquid food product decreases when it passes the inlet section; and introducing the liquid food product into the vacuum vessel.

The method for flash boiling liquid food product may be performed with the flash boiling apparatus previously described. The method may incorporate any of the features described in connection with the flash boiling apparatus, and vice versa, and share the corresponding advantages.

BRIEF DESCRIPTION OF THE DRAWINGS

Embodiments will now be described, by way of example, with reference to the accompanying schematic drawings, in which FIG. 1 is a side view of a flash boiling apparatus for a liquid food product that comprises particles, FIG. 2 is a top view of the flash boiling apparatus of FIG. 1, FIG. 3 is a cross-sectional view of an inlet section of the flash boiling apparatus of FIG. 1, as seen along line B-B in FIG. 2.

DETAILED DESCRIPTION

Figure 4:
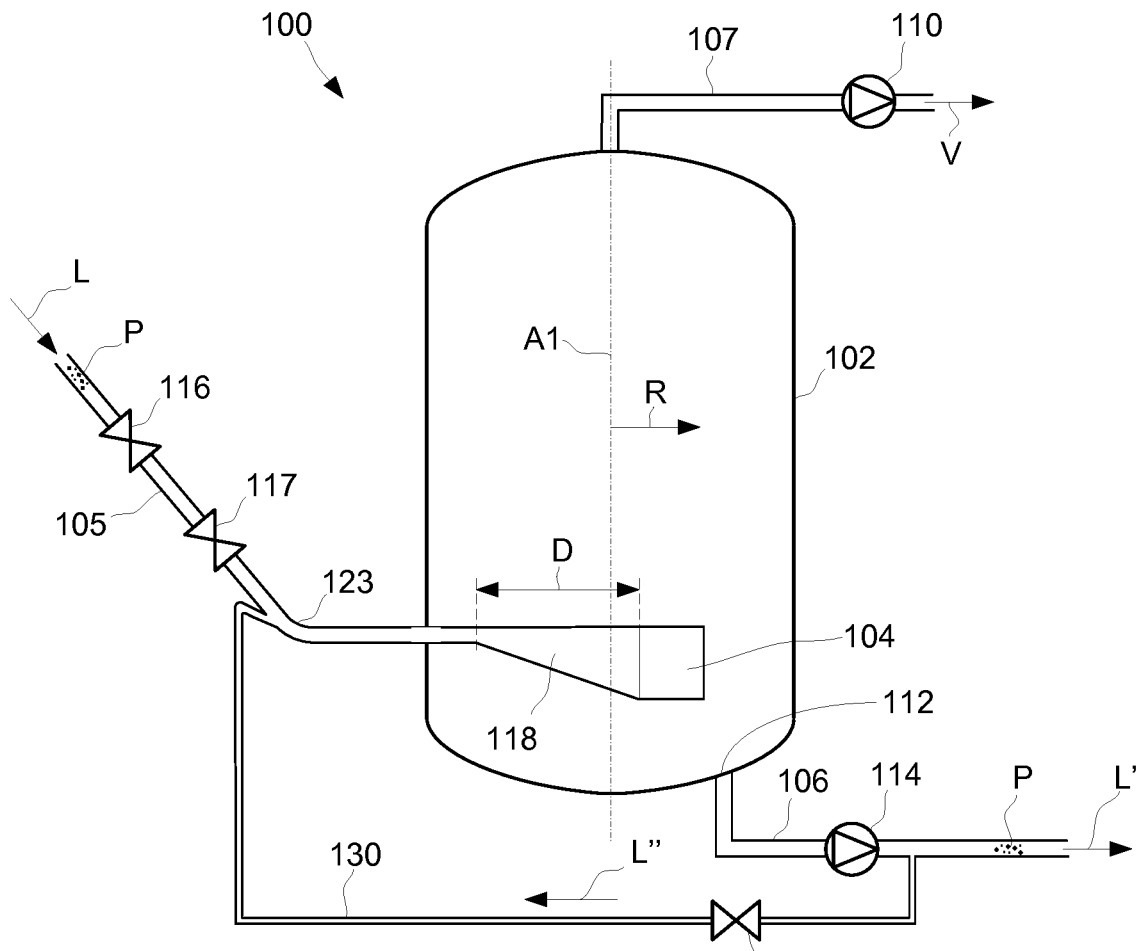
FIG. 4 is a side view of an embodiment of the flash boiling apparatus of FIG. 1, including a product return line.

With reference to FIGS. 1 and 2 an example of a flash boiling apparatus 100 is schematically illustrated. The flash boiling apparatus 100 comprises a vacuum vessel 102, a product inlet pipe 105, a product outlet pipe 106 and a vapour outlet pipe 107. The vacuum vessel 102 has a cylindrical shape that extends along a central cylinder axis A1. A direction R that is perpendicular to the cylinder axis A1 defines a radial direction of the vacuum vessel 102.

The product inlet pipe 105 supplies a liquid food product L that comprises particles P into the vacuum vessel 102 via a product inlet 104 of the vacuum vessel 102. A vacuum pump 110 is arranged in the vapour outlet pipe 107 for providing a low pressure in the vacuum vessel 102. The pressure in the product inlet pipe 105 is higher than the pressure in the vacuum vessel 102, such that flash boiling may occur when the liquid food product L enters the vacuum vessel 102.

The liquid food product L may be a diary based product, a soy based product, a beverage product or any other liquid food product. The particles P may be larger particles, such as berries, as well as smaller particles such as different kind of minerals, nutrition, seeds and grains.

Due to the flash boiling, some of the water in the product L forms vapour V, and gas entrapped in the product is released. Vapour V and gas can be fed out from the vacuum vessel 100 via the vapour outlet pipe 107 by using the vacuum pump 110. The vacuum pump 110 may in addition to feeding out vapour V and released gas provide for that the pressure inside the vacuum vessel 102 is kept within a pre-set range that accomplished the flash boiling. Liquid food product is collected in a lower part of the vacuum vessel 102, and can be fed out from the vacuum vessel 102 via a product outlet 112 to which the product outlet pipe 106 is connected. A pump 114 is arranged in the product outlet pipe 106 for feeding out outgoing liquid food product L' that comprises the particles P.

In order to control the flash boiling by providing for that there is a pressure drop between the product inlet pipe 105 and the vacuum vessel 102, a pressure relief valve 116, also referred to as a first pressure relief valve 116, is provided upstream the product inlet 104. The pressure relief valve 116 is a conventional pressure relief valve of a type that is used for flash boiling.

With further reference to FIG. 3, an inlet section 118 is arranged between the pressure relief valve 116 and the product inlet 104 to thereby convey the liquid food product L from the pressure relief valve 116 to the product inlet 104. The inlet section 118 forms a channel for the liquid food product L, and has a through-flow area 119 that increases in a direction from the pressure relief valve 116 to the product inlet 104. The direction from the pressure relief valve 116 to the product inlet 104 is the flow direction of the liquid food product L, from the pressure relief valve 116 to the product inlet 104.

Since the through-flow area 119 of the inlet section 118 increases in the flow direction of the liquid food product L, the flow velocity $v_{flow}$ of the liquid food product L decreases when it passes through the inlet section 118. The liquid food product L has then a reduced flow velocity when it enters the vacuum vessel 102 via the product inlet 104, which reduces wear that otherwise might arise when the liquid food product L hits the interior surface of the vacuum vessel 102.

The inlet section 118 might be given any geometrical shape that increases its through-flow area 119 in the flow direction of the liquid food product L. A part of the inlet section 118 or the full inlet section 118 may have a through-flow area 119 that increases in the flow direction of the liquid food product L.

The through-flow area 119 of the inlet section 118 increases, in the direction from the pressure relief valve 116 to the product inlet 104, i.e. in the flow direction of the liquid food product L, by at least a factor of 2. This means that if the smallest through-flow area 119 of the inlet section 118 is 30 cm$^2$, then the through-flow area 119 becomes at least 60 cm$^2$ (2 times 30 cm$^2$) before or at a point where the inlet section 118 is connected to the product inlet 104. Optionally, the through-flow area 119 of the inlet section 118 increases, in the direction from the pressure relief valve 116 to the product inlet 104, by at least a factor of 3, a factor of 6, a factor of 10, or by an even greater factor.

The through-flow area 119 of the inlet section 118 may increases along a distance D of 0 cm to 10 cm. Thus, the full increase of the through-flow area 119 according to any of the above exemplified factors take place over the distance D of 0 cm to 10 cm. It is possible that the through-flow area 119 is increased before or after the distance D over which the through-flow area 119 is increased. However, the factor that defines the increase of the through-flow area 119 is still determined over the distance D. The distance D of 0 cm to 10 cm is relatively short, which assists in effectively reducing the flow velocity $v_{flow}$ of the liquid food product L.

For a distance of 0 cm the through-flow area 119 increases rapidly with a sharp boundary defining the increase. This may be implemented by connecting one smaller pipe to a larger pipe via a disk. Such a disk may have a central hole that is defined by an inner peripheral edge to which the smaller pipe is attached. The larger pipe is then connected to the outer, peripheral edge of the disk.

The through-flow area 119 of the inlet section 118 may increase along a longer distance, such as a distance D of 10 cm to 40 cm, or a distance D of 10 cm to 70 cm, or even over a longer distance.

The through-flow area 119 of the inlet section 118 may have a rectangular shape, either in full or partially. Generally, the shape of the through-flow area 119 may be circular at first to then transform into a rectangular shape, as seen in the flow direction of the liquid food product L. The illustrated shape (see FIG. 3) has sharp corners. However, the corners may be rounded.

As mentioned, the vacuum vessel 102 may have a cylindrical shape that extends along a central cylinder axis A1. The through-flow area 119 of the inlet section 118 may have a first side 120 that extends in parallel to the cylinder axis A1, and a second side 121 that extends in a direction R that is perpendicular to the cylinder axis A1. The second side 121 is shorter than the first side 120.

The inlet section 118 may comprises a bend 123. The bend 123 may have a bend angle α of 35° to 55°. The bend 123 assists in slowing down the liquid food product L on its way from the pressure relief valve 116 to the product inlet 104 of the vacuum vessel 102.

A second pressure relief valve 117 may be arranged between the first pressure relief valve 116 and the inlet section 118. In operation, in the product inlet pipe 105 the liquid food product L has, as seen in its flow direction towards the vacuum vessel 102, a first pressure before the first pressure relief valve 116, a second pressure between the first pressure relief valve 116 and the second pressure relief valve 117, and a third pressure after the second pressure relief valve 117. The first pressure is higher than the second pressure, and the second pressure is higher than the third pressure. The third pressure is typically the same as or very close to the pressure inside the vacuum vessel 102.

Two serial pressure relief valves 116, 117 reduce the pressure of the liquid food product L in two steps, which is advantageous in that wear caused on the vacuum vessel 102 by the liquid food product L may be reduced.

With reference to FIG. 4 a product return line 130 may be is connected to the inlet section 118 for feeding liquid food product L" that previously has passed the inlet section 118 back into the inlet section 118. Only a part of the outgoing liquid food product L' is returned, or fed back, through the product return line 130. How much returned liquid food product L" is fed back to the inlet section 118 may be controlled by a valve 131.

The liquid food product L" that is fed back into the inlet section 118 is introduced in the inlet section 118 in a direction that coincides with a flow direction of liquid food product L that comes from the pressure relief valve 116, or comes from pressure relief valve 117 in case two pressure relief valves are used. The product return line 130 extends from the product outlet pipe 106 to the product inlet pipe 105, and may be connected to the product inlet pipe 105 where the bend 123 is located. It may also be said the product return line 130 is connected to the inlet section 118, since the inlet section 118 comprise or form part the product inlet pipe 105.

By introducing the returned liquid food product L" in a direction that coincides with a flow direction of liquid food product L, the returned food product L" may create a protective film at the location where it is introduced. Introducing the returned liquid food product L" at the bend is advantageous since the bend 123 is subjected to a relatively higher wear.

Figure 5:
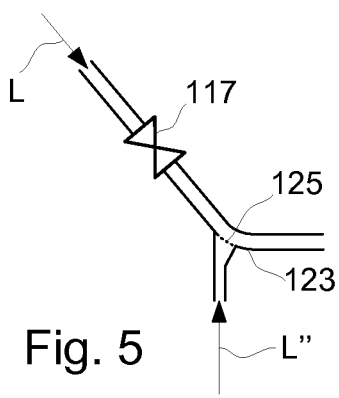
FIG. 5 is a partial view of an alternative embodiment of a product return line that may be used for the flash boiling apparatus of FIG. 1.

With reference to FIG. 5 the liquid food product L" that is fed back into the inlet section 118 may be introduced in the inlet section 118 via a number of openings 125 that form a perforated inlet into the inlet section 118. These opening may be arranged at the bend 123.

Figure 6:
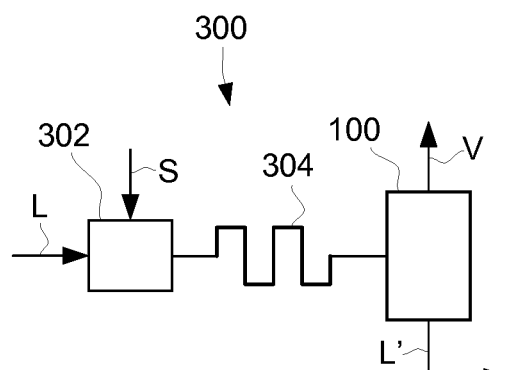
FIG. 6 is a schematic illustration of a food processing system that comprises the flash boiling apparatus of FIG. 1.

With reference to FIG. 6 a food processing system 300 for processing a liquid food product L that comprises particles P is illustrated. The system 300 comprises a conventional steam injection device 302 and a conventional holding cell 304 for heat treating the product L. The steam injection device 302 injects steam S into the liquid food product liquid food product L and the product L passes through the holding cell 304 during a few seconds. This accomplishes heat treatment of the liquid food product L. The heat treatment kills or at least reduces microorganisms in the product L to an extent where the number of viable pathogens in the product L is so low that they are unlikely to cause disease, as long as the product is stored as prescribed and is consumed before its expiration date. The system 300 also includes the flash boiling apparatus 100 described above, for removing steam (vapour) V that was injected by the steam injection device 302 and for outputting a heat treated product L'.

Figure 7:
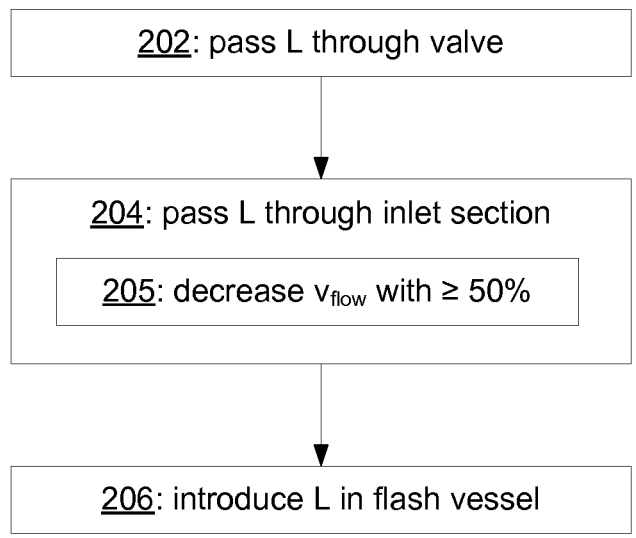
FIG. 7 is a flow chart of a method for flash boiling a liquid food product that comprises particles.

With reference to FIG. 7 a method for flash boiling a liquid food product L that comprises particles P is illustrated. The method may be performed on, for example, the flash boiling apparatus 100 previously described.

The method comprises passing 202 the liquid food product L through the pressure relief valve 116, which is arranged upstream the product inlet 104 of the vacuum vessel 102. For realizing this passing 202 a conventional pump (not shown) is typically arranged upstream the pressure relief valve 116. When the liquid food product L passes the pressure relief valve 116 a pressure drop is provided for the liquid food product L, which results in flash boiling of the liquid food product L once it is introduced in the vacuum vessel 102.

After the pressure relief valve 116 the liquid food product L is passed 204 through the inlet section 118 that is arranged between the pressure relief valve 116 and the product inlet 104 of the vacuum vessel 102. Since the inlet section 118 has a through-flow area 119 that increases in the direction from the pressure relief valve 116 to the product inlet 104, the flow velocity $v_{flow}$ of the liquid food product L is decreased as it passes the inlet section 118.

Finally, the liquid food product L is introduced 206 into the vacuum vessel 102, where the liquid food product L is flash boiled.

The passing 204 of the liquid food product L through the inlet section 118 may comprise decreasing 205 the flow velocity $v_{flow}$ of the liquid food product L by at least 50%. This percentage is determined based on the difference in the flow velocity of the liquid food product L before the inlet section 118 and after the inlet section 118. The 50% decrease of the flow velocity is accomplished by increasing the through-flow area 119 in the direction from the pressure relief valve 116 to the product inlet 104. Exactly how much the through-flow area 119 should be increased for obtaining a desired flow velocity decrease may be empirically determined.

The flash boiling apparatus 100 may be used in a number of different applications for removing vapour. An example of an application is when water was introduced in the product during heat treatment by using steam injection, and where the introduced water must be removed so that the product does not become diluted.

More particularly, during the heat treatment steam can be injected such that a temperature of the product is increased from 80° C. to 140° C. After the product has been heated, it is kept at this temperature for a predetermined period of time, such as about 4 seconds, and is then quickly cooled down to 80° C. In order to remove vapour introduced during the steam injection as well as for cooling (flash cooling) the product, the flash boiling apparatus 100 can be used.

Another application area for the apparatus 100 is to use it as a deaerator, where only gas is removed from the product. Then a condenser may be provided in order to ensure that liquid product transformed into vapour during the flash boiling is transformed back into liquid that drops down into and joins the product. The vapour outlet pipe 107 is then replaced by gas outlet pipe.

From the description above follows that, although various embodiments of the invention have been described and shown, the invention is not restricted thereto, but may also be embodied in other ways within the scope of the subject-matter defined in the following claims. In particular, the inlet section may be given many different shapes that accomplish the increase of the through-flow area in the direction from the pressure relief valve to the product inlet.

The invention claimed is:

1. A flash boiling apparatus for a liquid food product that comprises particles, said flash boiling apparatus comprising:
   a vacuum vessel provided with a product inlet for incoming liquid food product and a product outlet for outgoing liquid food product,
   a pressure relief valve arranged upstream the product inlet, for providing a pressure drop that results in flash boiling of the incoming liquid food product, and an inlet section arranged between the pressure relief valve and the product inlet, for conveying the liquid food product from the pressure relief valve to the product inlet, wherein the inlet section comprises a through-flow area that increases in a direction from the pressure relief valve to the product inlet, such that a flow velocity of the liquid food product decreases when it passes the inlet section, and the flash boiling apparatus further comprises a product return line that is connected to the inlet section for feeding the liquid food product that previously has passed the inlet section back into the inlet section.

2. The flash boiling apparatus according to claim 1, wherein the through-flow area of the inlet section increases, in the direction from the pressure relief valve to the product inlet, by at least a factor of 3.

3. The flash boiling apparatus according to claim 1, wherein the through-flow area of the inlet section increases, in the direction from the pressure relief valve to the product inlet, by at least a factor of 6.

4. The flash boiling apparatus according to claim 1, wherein the through-flow area of the inlet section increases along a distance of 0 cm to 10 cm.

5. The flash boiling apparatus according to claim 1, wherein the through-flow area of the inlet section increases along a distance of 10 cm to 40 cm.

6. The flash boiling apparatus according to claim 1, wherein the through-flow area of the inlet section comprises a rectangular shape.

7. The flash boiling apparatus according to claim 1, wherein the vacuum vessel comprises a cylindrical shape that extends along a central cylinder axis, and the through-flow area of the inlet section has a first side that extends in parallel to the cylinder axis, and a second side that is shorter than the first side and extends in a direction that is perpendicular to the cylinder axis.

8. The flash boiling apparatus according to claim 1, wherein the inlet section comprises a bend.

9. The flash boiling apparatus according to claim 8, wherein the bend has a bend angle of 35° to 55°.

10. The flash boiling apparatus according to claim 1, wherein the liquid food product that is fed back into the inlet section is introduced in the inlet section in a direction that coincides with a flow direction of liquid food product that comes from the pressure relief valve.

11. The flash boiling apparatus according to claim 1, wherein the liquid food product that is fed back into the inlet section is introduced in the inlet section via a number of openings that form a perforated inlet into the inlet section.

12. The flash boiling apparatus according to claim 1, wherein the pressure relief valve is a first pressure relief valve, and a second pressure relief valve is arranged between the first pressure relief valve and the inlet section.

13. A food processing system comprising a steam injection device, a holding cell and the flash boiling apparatus according to claim 1.

14. A method for flash boiling a liquid food product that comprises particles, said method comprising:

passing liquid food product through a pressure relief valve arranged upstream a product inlet of a vacuum vessel, for providing a pressure drop that results in flash boiling of the liquid food product when the liquid food product is introduced in the vacuum vessel, passing the liquid food product through an inlet section that is arranged between the pressure relief valve and the product inlet, and comprises a through-flow area that increases in a direction from the pressure relief valve to the product inlet, such that a flow velocity of the liquid food product decreases when it passes the inlet section, introducing the liquid food product into the vacuum vessel, and feeding the liquid food product that previously has passed the inlet section back into the inlet section by a product return line that is connected to the inlet section.

15. The method according to claim 14, wherein the passing the liquid food product through the inlet section comprises:

decreasing the flow velocity of the liquid food product by at least 50%.

* * * * *